(12) United States Patent
Novak, Jr.

(10) Patent No.: US 11,259,745 B2
(45) Date of Patent: Mar. 1, 2022

(54) AUTONOMOUS DRUG DELIVERY SYSTEM

(71) Applicant: MASIMO CORPORATION, Irvine, CA (US)

(72) Inventor: Jerome J. Novak, Jr., Lake Forest, CA (US)

(73) Assignee: MASIMO CORPORATION, Irvine, CA (US)

( * ) Notice: Subject to any disclaimer, the term of this patent is extended or adjusted under 35 U.S.C. 154(b) by 201 days.

(21) Appl. No.: 15/909,359

(22) Filed: Mar. 1, 2018

(65) Prior Publication Data

US 2018/0317841 A1 Nov. 8, 2018

Related U.S. Application Data

(63) Continuation-in-part of application No. 14/608,188, filed on Jan. 28, 2015, now Pat. No. 10,086,138.
(Continued)

(51) Int. Cl.
*A61B 5/00* (2006.01)
*A61B 5/021* (2006.01)
(Continued)

(52) U.S. Cl.
CPC ............ *A61B 5/4839* (2013.01); *A61B 5/021* (2013.01); *A61B 5/746* (2013.01); *A61M 5/14* (2013.01);
(Continued)

(58) Field of Classification Search
CPC ....... A61B 5/4839; A61B 5/746; A61B 5/021; A61B 5/0402; A61B 5/0015; G16H 40/67; G16H 50/50; G16H 40/63; G16H 50/20; G16H 40/20; G16H 20/17; A61M 5/1723; A61M 5/142; A61M 5/14; A61M 2205/3569; A61M 2205/3507; A61M 2205/3584; A61M 2205/3561; A61M 2205/3592; A61M 2205/3553;
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

WO WO2007/033025 A2 3/2007
WO WO 2019/169026 9/2019

OTHER PUBLICATIONS

US 9,579,050 B2, 02/2017, Al-Ali (withdrawn)
(Continued)

*Primary Examiner* — James D Ponton
(74) *Attorney, Agent, or Firm* — Knobbe, Martens, Olson & Bear, LLP

(57) ABSTRACT

An autonomous drug delivery system advantageously utilizes physiological monitor outputs so as to automatically give a bolus of a rescue drug or other necessary medication when certain criteria and confidence levels are met. An emergency button is provided to manually trigger administration of the rescue drug. The rescue drug may be an opioid antagonist in response to an analgesia overdose, a hypotensive drug to avert an excessive drop in blood pressure or an anti-arrhythmia drug to suppress abnormal heartbeats, to name a few.

21 Claims, 12 Drawing Sheets

Related U.S. Application Data

(60) Provisional application No. 61/932,437, filed on Jan. 28, 2014.

(51) Int. Cl.

| | | |
|---|---|---|
| *G16H 20/17* | (2018.01) | |
| *A61M 5/14* | (2006.01) | |
| *A61M 5/168* | (2006.01) | |
| *G16H 40/20* | (2018.01) | |
| *G16H 50/20* | (2018.01) | |
| *G16H 40/63* | (2018.01) | |
| *G16H 50/50* | (2018.01) | |
| *A61M 5/142* | (2006.01) | |
| *A61M 5/172* | (2006.01) | |
| *G16H 40/67* | (2018.01) | |
| *A61B 5/318* | (2021.01) | |

(52) U.S. Cl.
CPC ............ *A61M 5/142* (2013.01); *A61M 5/168* (2013.01); *A61M 5/1723* (2013.01); *G16H 20/17* (2018.01); *G16H 40/20* (2018.01); *G16H 40/63* (2018.01); *G16H 40/67* (2018.01); *G16H 50/20* (2018.01); *G16H 50/50* (2018.01); *A61B 5/0015* (2013.01); *A61B 5/318* (2021.01); *A61M 2005/1405* (2013.01); *A61M 2205/18* (2013.01); *A61M 2205/3303* (2013.01); *A61M 2205/3507* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/581* (2013.01)

(58) Field of Classification Search
CPC ...... A61M 2205/502; A61M 2205/581; A61M 2205/50; A61M 2005/1405; A61M 2205/3303; A61M 2205/18; A61M 5/168
See application file for complete search history.

(56) References Cited

U.S. PATENT DOCUMENTS

| | | | |
|---|---|---|---|
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,987,343 | A | 11/1999 | Kinast |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,067,466 | A * | 5/2000 | Selker .................. A61B 5/0452 600/513 |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,115,673 | A | 9/2000 | Malin et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |

(56) References Cited

U.S. PATENT DOCUMENTS

| | | |
|---|---|---|
| 6,383,136 B1 * | 5/2002 | Jordan ............ G06F 19/3418 600/300 |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,297,113 B1 * | 11/2007 | Russell ............ A61B 5/145 600/302 |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B2 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |

(56) References Cited

U.S. PATENT DOCUMENTS

| | | |
|---|---|---|
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |

(56) References Cited

U.S. PATENT DOCUMENTS

| | | |
|---|---|---|
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |

(56) References Cited

U.S. PATENT DOCUMENTS

| | | |
|---|---|---|
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Tanaka et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2002/0151816 A1* | 10/2002 | Rich ............... A61B 5/0031 600/547 |

(56) References Cited

U.S. PATENT DOCUMENTS

| | | |
|---|---|---|
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0161744 A1 | 8/2003 | Vilks et al. |
| 2003/0212312 A1 | 11/2003 | Coffin et al. |
| 2003/0212379 A1 | 11/2003 | Bylund et al. |
| 2004/0106163 A1 | 6/2004 | Workman, Jr. et al. |
| 2004/0117204 A1* | 6/2004 | Mazar ............ A61B 5/0031 705/2 |
| 2005/0055276 A1 | 3/2005 | Kiani et al. |
| 2005/0182389 A1* | 8/2005 | LaPorte ........... A61B 5/0031 604/890.1 |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0062730 A1 | 3/2009 | Woo |
| 2009/0069787 A1 | 3/2009 | Estes et al. |
| 2009/0093687 A1 | 4/2009 | Telfort et al. |
| 2009/0095926 A1 | 4/2009 | MacNeish |
| 2009/0149839 A1* | 6/2009 | Hyde ............... A61B 1/041 604/890.1 |
| 2009/0247984 A1 | 10/2009 | Lamego et al. |
| 2009/0259217 A1 | 10/2009 | Hyde et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0081942 A1* | 4/2010 | Huiku ............. G16H 40/60 600/483 |
| 2010/0099964 A1 | 4/2010 | O'Reilly et al. |
| 2010/0185143 A1 | 7/2010 | Uhland et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0152651 A1* | 6/2011 | Berkow ............ A61B 5/412 600/324 |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0185267 A1* | 7/2012 | Kamen ............ G06F 19/3418 705/2 |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0259282 A1 | 10/2012 | Alderete, Jr. et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0331778 A1 | 12/2013 | Kruse et al. |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0309615 A1 | 10/2014 | Mazlish |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |

(56) References Cited

U.S. PATENT DOCUMENTS

| | | |
|---|---|---|
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0367071 A1 | 12/2015 | Donnellan et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0008146 A1 | 1/2018 | Al-Ali et al. |
| 2018/0103874 A1 | 4/2018 | Lee et al. |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Mushin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0058280 A1 | 2/2019 | Al-Ali et al. |
| 2019/0058281 A1 | 2/2019 | Al-Ali et al. |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0320988 A1 | 10/2019 | Ahmed et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |

OTHER PUBLICATIONS

Drug Overdose, Wikipedia, printed on Feb. 8, 2018, 8 pages, https://enwikipedia.org/wiki/Drug_overdose.

Hypovolemia, Wikipedia, printed on Feb. 8, 2018, 6 pages, https://en.wikipedia.org/wiki/Hypovolemia.

Sepsis, Wikipedia, printed on Feb. 8, 2018, 26 pages, https://en.wikipedia.org/wiki/Sepsis.

Apr. 23, 2019 PCT International Search Report in PCT/US2019/019885.

* cited by examiner

AUTONOMOUS DRUG DELIVERY SYSTEM

INCORPORATION BY REFERENCE TO ANY RELATED APPLICATIONS

Any and all applications, if any, for which a foreign or domestic priority claim is identified in the Application Data Sheet of the present application are hereby incorporated by reference under 37 CFR 1.57.

BACKGROUND

Pulse oximetry is a widely accepted noninvasive procedure for measuring the oxygen saturation level of arterial blood, an indicator of a person's oxygen supply. A typical pulse oximetry system utilizes an optical sensor attached to a fingertip to measure the relative volume of oxygenated hemoglobin in pulsatile arterial blood flowing within the fingertip. Oxygen saturation (SpO2), pulse rate and a plethysmograph waveform, which is a visualization of pulsatile blood flow over time, are displayed on a monitor accordingly.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entirety by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entirety by reference herein. Advanced pulse oximetry systems including Masimo SET® low noise optical sensors and read through motion pulse oximetry monitors for measuring SpO2, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entirety by reference herein. Advanced blood parameter measurement systems include Masimo Rainbow® SET, which provides measurements in addition to SpO2, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF CERTAIN EMBODIMENTS

Hospital patients and out-patients may experience negative effects from various pharmaceutical drugs prescribed for treatment. These negative effects may be due to overdose, under dose or adverse reactions to these drugs. As one example, opioids are often given to post-surgical patients for pain management, and while opioid use is safe for most patients, opioid analgesics are often associated with adverse reactions, such as respiratory depression as a result of excessive dosing, improper monitoring, medication interactions and adverse reactions with other drugs. Complications from opioid use are inevitable and not always avoidable. However, when a patient dies because such complications were not timely recognized or treated appropriately, it is termed a "failure to rescue."

Failure to rescue in the case of opioid overdose can be largely prevented by an advantageous autonomous administration of an opioid antagonist. Similarly, other serious patient conditions such as heart arrhythmia, high or low heart rate, high or low blood pressure, hypoglycemia and anaphylactic shock, to name a few, may be moderated by the autonomous administration of an appropriate rescue drug. An autonomous drug delivery system (ADDS) advantageously utilizes physiological monitor outputs so as to automatically give at least one bolus of at least one drug or medicine when certain criteria and confidence levels are met. In addition, an emergency button is provided to manually trigger administration of such a rescue drug or medicine. In an embodiment, the emergency button may be triggered remotely. ADDS advantageously responds with a rescue drug when delay in clinician response would otherwise result in patient injury or death.

One aspect of an autonomous drug delivery system is a housing with a front panel and a drug compartment. A display and buttons are disposed on the front panel. An IV injector is disposed in the drug compartment, and a nozzle extending from the housing is in mechanical communications with the IV injector. In an embodiment, the IV injector has a drug reservoir, a piston partially disposed within and extending from the drug reservoir and a drive motor in mechanical communications with the piston. The drive motor actuates so as to drive the piston against a drug containing bolus disposed within the drug reservoir. The piston causes the drug to extrude from the nozzle.

Another aspect of an autonomous drug delivery system is receiving a physiological parameter indicative of a medical state of a person and calculating a trigger condition and a corresponding confidence indicator. An alarm occurs if the trigger condition exceeds a predetermined threshold. A drug is administered to the person if the alarm is not manually acknowledged within a predetermined time interval.

DETAILED DESCRIPTION

Figure 1A:
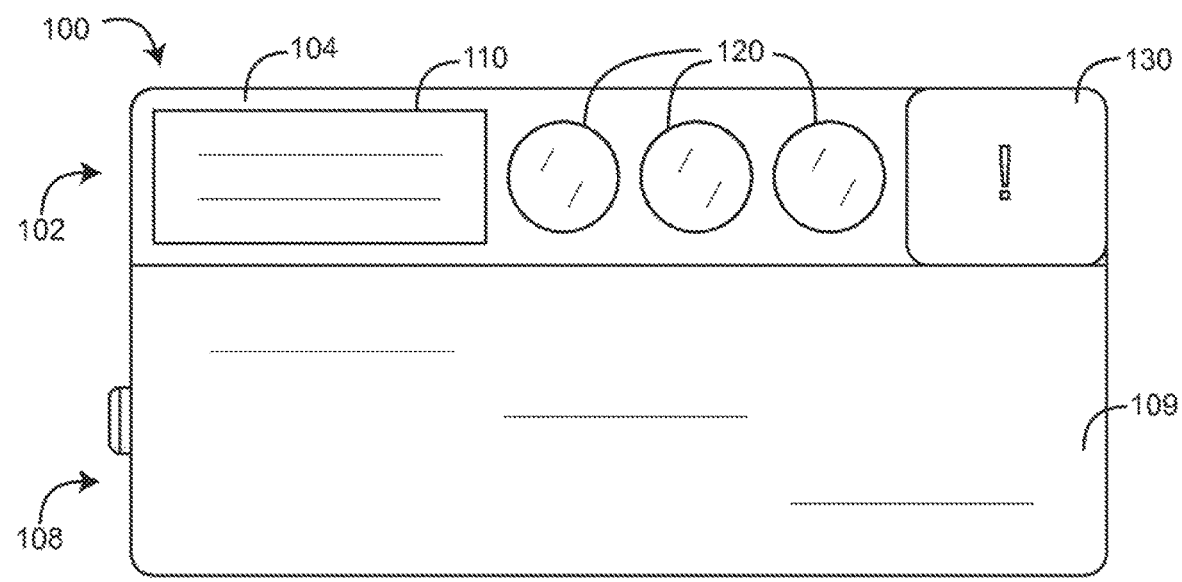
FIGS. 1A-C are front, front partial-cutaway, and cutaway drug reservoir views of an autonomous drug delivery system (ADDS) embodiment.
Figure 1B:
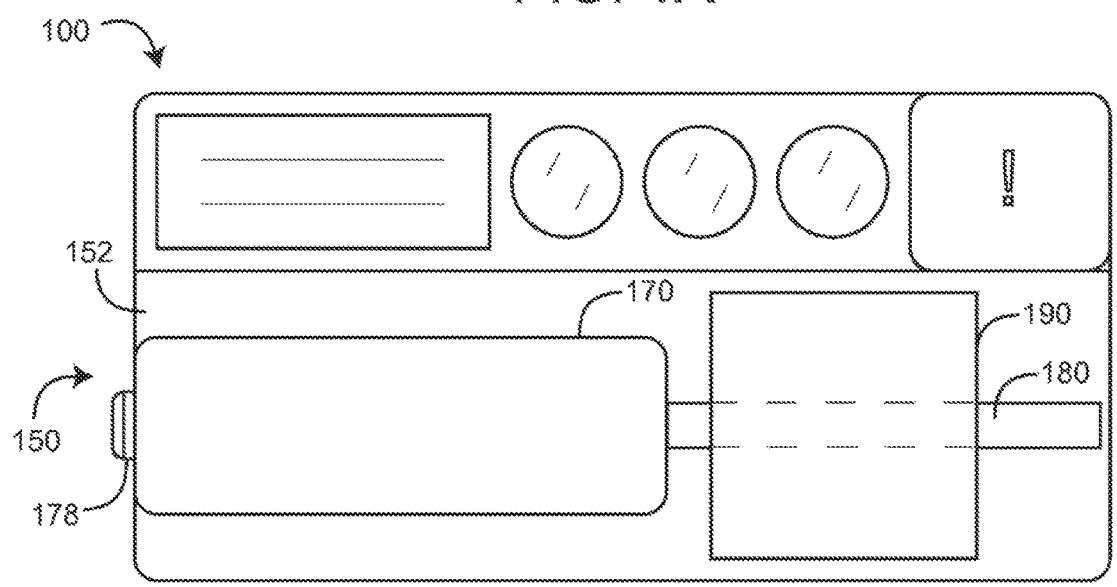
Figure 1C:
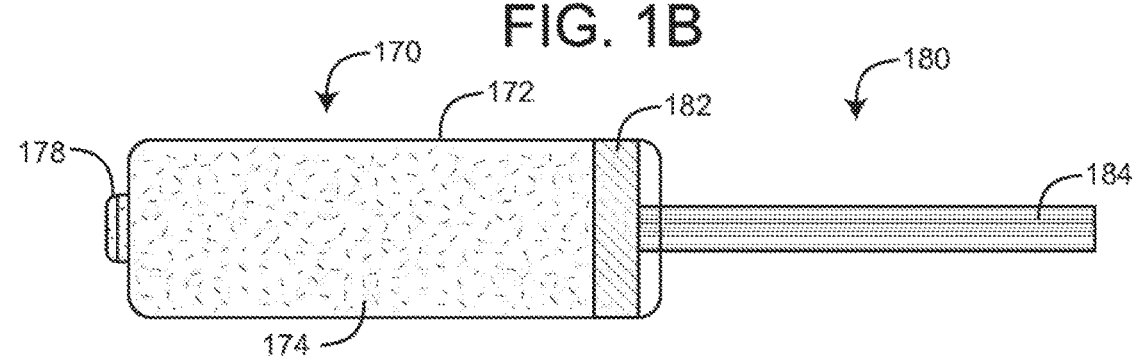

FIGS. 1A-C illustrate an autonomous drug delivery system (ADDS) 100 that inputs physiological parameters generated by one or more patient monitors, such as SpO2, PR, RR, EtCO2 and BP, and evaluates certain criteria and confidence levels based upon those parameters, so as to automatically give a bolus of a rescue drug. As shown in FIG. 1A, the autonomous drug delivery system 100 has a control section 102 and a drug section 108. The control section 102 has a front panel 104 and an electrical interface (not visible). The front panel 104 provides a user interface including a user display 110, such as an LED or LCD readout of device and patient status, among other data; control buttons 120 such as power on/off, reset, mode among other functions, and an emergency button 130 to manually trigger administration of the rescue drug. The emergency button 130 may have a flip-up cover or other safety mechanism, such as a simultaneous press with another button, so as to prevent inadvertent drug administration. The electrical interface communicates with patient monitor(s), alarm(s) and the drug section 108. The drug section 108 has a cover 109 concealing a drug administration device installed within a recessed compartment, described below.

As shown in FIG. 1B, the cover 109, once flipped-up, slid-open, removed or otherwise opened, exposes an IV injector 150 having a drug reservoir 170, a piston 180 and a drive motor 190 disposed within a drug compartment 152. The drug reservoir 170 is configured to accept a disposable bolus of a rescue drug. When actuated, the motor 190 drives the piston 180 into the drug reservoir 170 so that the rescue drug contained in the drug reservoir 170 is expelled out of the nozzle 178 (FIG. 1C) and into an attached IV tube that carries the rescue drug to the patient, as described with respect to FIGS. 2-3, below. The bolus remains in the drug reservoir 170 until it is used or expires. The expiration date can optionally be read from the bolus or otherwise entered into the ADDS memory (part of the DSP 810 FIG. 8)

As shown in FIG. 1C, in a ready position, the drug reservoir 170 has a generally-cylindrical enclosure 172 containing an unused rescue drug 174 and a piston 180. In particular, the piston 180 has a piston head 182 disposed within the enclosure 172 and a piston shaft 184 extending from the enclosure 172. The motor acts on the piston shaft 184 so as to move the piston head 182 from a first position (shown) distal the nozzle 178 to a second position proximate the nozzle, thus expelling the rescue drug from the reservoir 170 and into an IV tube (not shown) attached to the nozzle 178.

Figure 2:
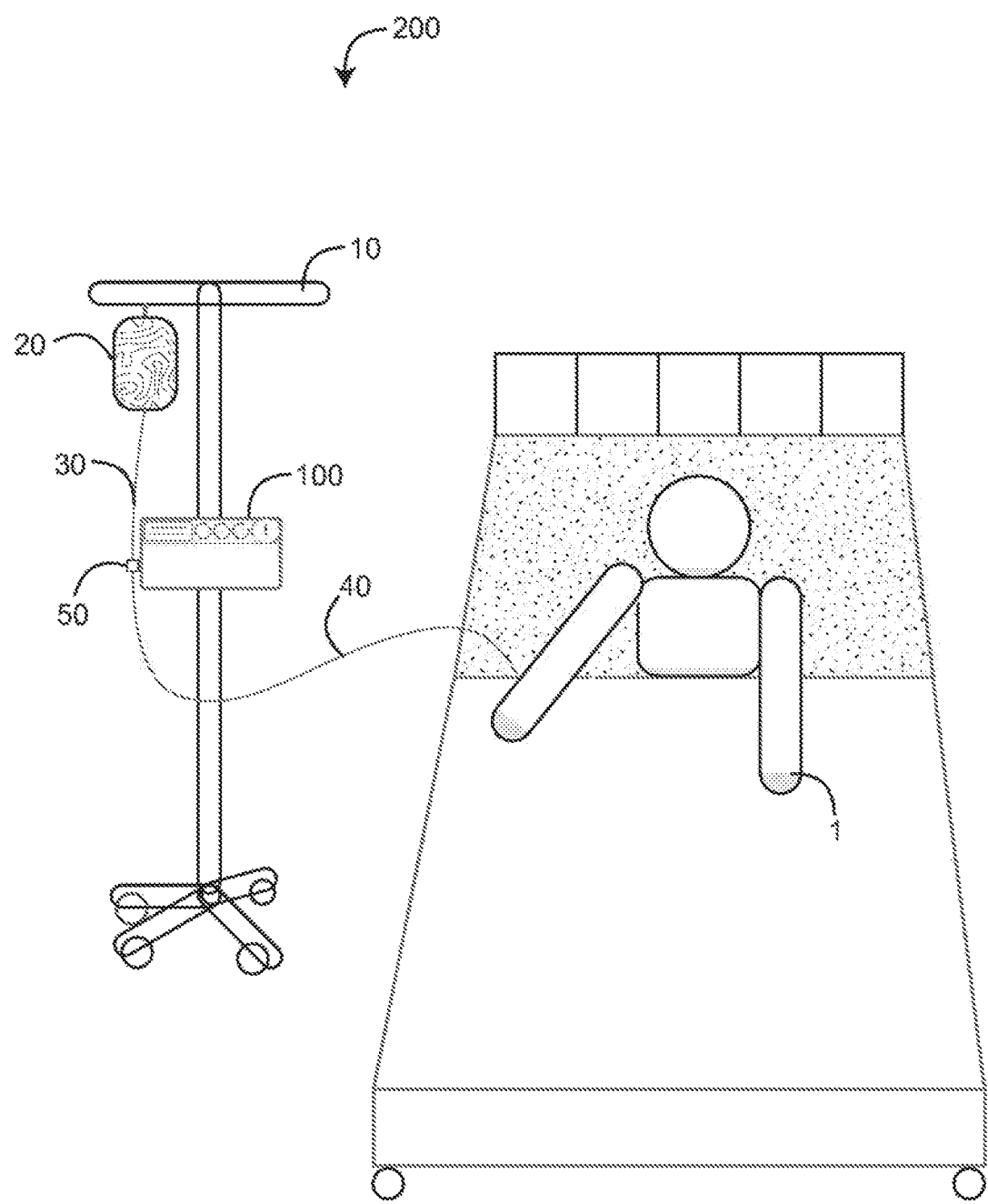
FIG. 2 is a front view of an autonomous drug delivery system configured with a conventional IV drip.

FIG. 2 illustrates a conventional IV drip configuration 200 incorporating an autonomous drug delivery system 100. In particular, an IV pole 10 mounts an IV bag 20 in fluid communications with a patient 1 via an IV line 30. Splicing the IV line is a one-way valve 50 in communications with the ADDS 100 via a line shunt 40. In the event the ADDS 100 is triggered, either manually via the emergency button 130 (FIG. 1A) or automatically via patient monitor inputs in communications with the control section 102 (FIG. 1A), the ADDS 100 injects its rescue drug 174 (FIG. 1C) into the shunt 40 and into the IV line 30 via the one-way valve 50, which shuts off the IV bag drip 20 blocking further IV bag 20 fluid.

Figure 3:
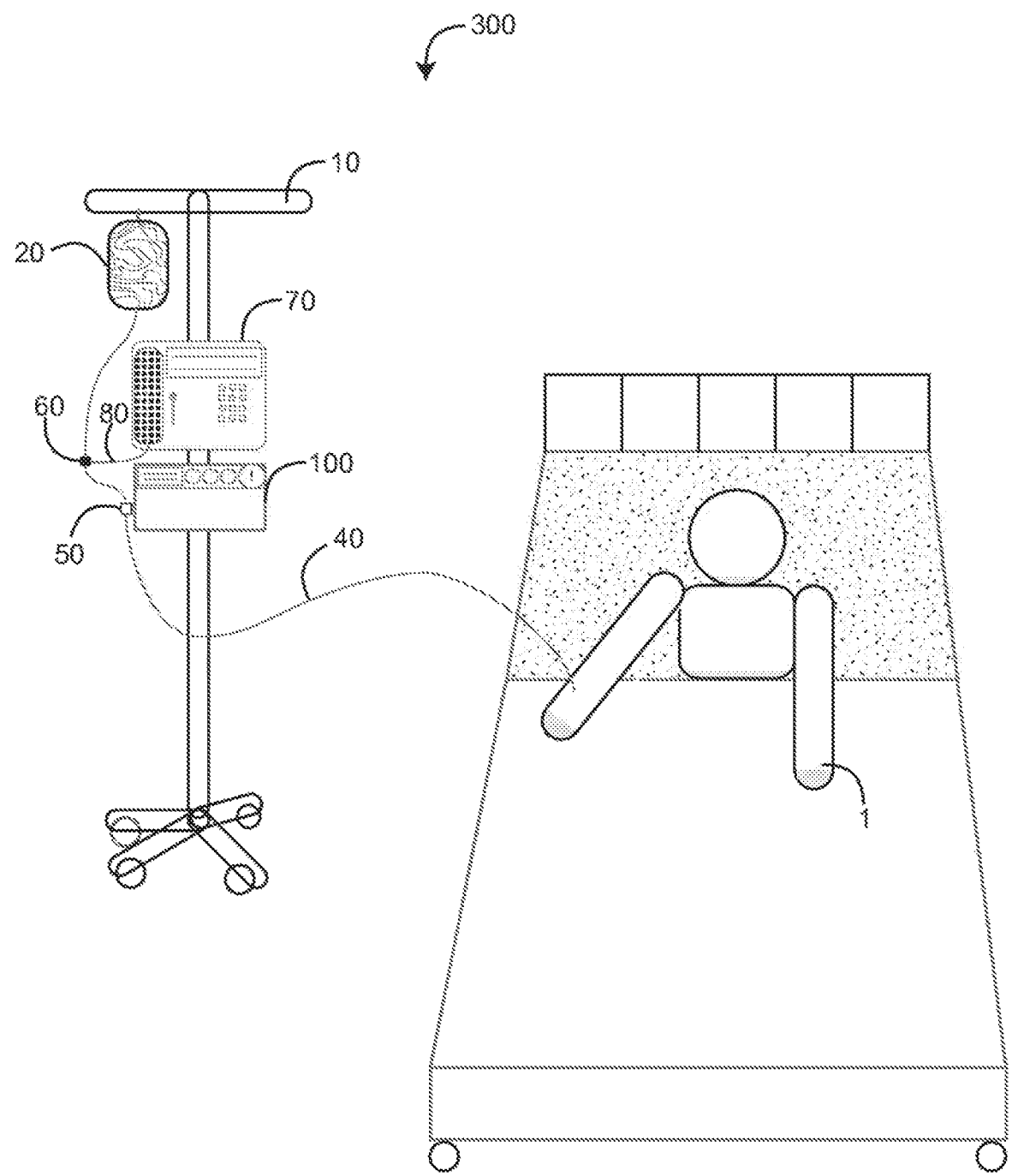
FIG. 3 is a front view of an autonomous drug delivery system configured with an IV drip and a patient controlled analgesia (PCA) pump.

FIG. 3 illustrates another conventional IV drip configuration 300 incorporating an autonomous drug delivery system 100 in addition to a patient controlled analgesia (PCA) pump 70. Similar to the FIG. 2 configuration described above, an IV pole 10 mounts an IV bag 20 in fluid communications with a patient 1 via an IV line 30. Splicing the IV line is a one-valve 50 in communications with the rescue device 100 via a line shunt 40. Also splicing the IV line is a one-valve 60 in communications with the PCA pump. As described above, in the event the ADDS 100 is triggered, either manually via the emergency button 130 (FIG. 1A) or automatically via patient monitor inputs in communications with the control section 102 (FIG. 1A), the ADDS 100 injects its rescue drug 174 (FIG. 1C) into the shunt 40 and into the IV line 30 via the one-way valve 50, which shuts off the IV bag drip 20 and the PCA analgesia 72.

The ADDS 100 may be used for a variety of medical emergencies and conditions in conjunction with a variety of rescue drugs. In one embodiment, the ADDS is advantageously used in conjunction with a patient controlled analgesia (PCA) device that delivers pain medication upon patient demand. For example, a patient can push a button to request a morphine injection. Here, a patient is particularly vulnerable to inadvertently overdosing themselves to the point of respiratory failure. The ADDS inputs one or more parameters such as respiration rate, oxygen saturation, pulse rate, blood pressure and end-tidal CO2 according to sensors attached to the patient and corresponding monitors and delivers an opioid antagonist such as Naloxone (Narcan), as described in further detail with respect to FIG. 4, below.

The ADDS 100 can optionally be responsive to heart arrhythmias and deliver a rescue drug specific to the type of rhythm detected; can optionally be responsive to a high heart rate or low heart rate so as to deliver a heart rate regulating drug; can optionally be responsive to high or low blood pressure so as to deliver a blood pressure regulating drug; can optionally be responsive to hypoglycemia so as to deliver glucagon; or can be responsive to other specific conditions and deliver appropriate medicine. In various embodiments, the ADDS 100 delivers compounded (mixed) formulas of more than one drug. This is accomplished through a mixture of drugs stored in a single reservoir or the use of multiple reservoirs. In all of these embodiments, the response is always a bolus (reservoir) administration. The drug is infused in a single administration step all at once (as opposed to over a prescribed amount of time as in a pump). The ADDS is capable of delivering multiple bolus doses, where subsequent bolus doses are ideally enabled after manual review of the initial, automatically delivered dose.

The ADDS can be configured to administer the bolus at a specific date and time, rather than in response to a monitored condition. The bolus administration can be at multiple discrete times or over a specified time interval. When the ADDS is responsive to multiple physiological parameters received from one or more monitoring instruments, a prescribed minimum and or maximum interval from a previous dose or start time may be used.

In various situations, physiological "guard rails" must be maintained. (See, for example FIGS. 6-7). As an example, a hypotensive drug may be used to raise a patient's blood pressure during emergencies. As another example, a drug to regulate heart rhythm or suppress arrhythmias may be used. In an embodiment, the display 110 (FIG. 1A) indicates the device is working and receiving proper inputs. The ADDS 100 has a memory that records data that can be recalled to indicate a trigger cause for administering a rescue drug, such as the time and amount of drug administered and other logged conditions. In an embodiment, the rescue drug is administered in a progression rather than all-at-once. For example, a 10% dose may be given and the patient monitored for improvement, with additional doses spaced at intervals as needed. In an embodiment, a spring driven piston with a releasable catch is used to administer the rescue drug in lieu of a motor-driven piston. In an embodiment, an ADDS is advantageously integrated with a PCA device as a single instrument.

Figure 4:
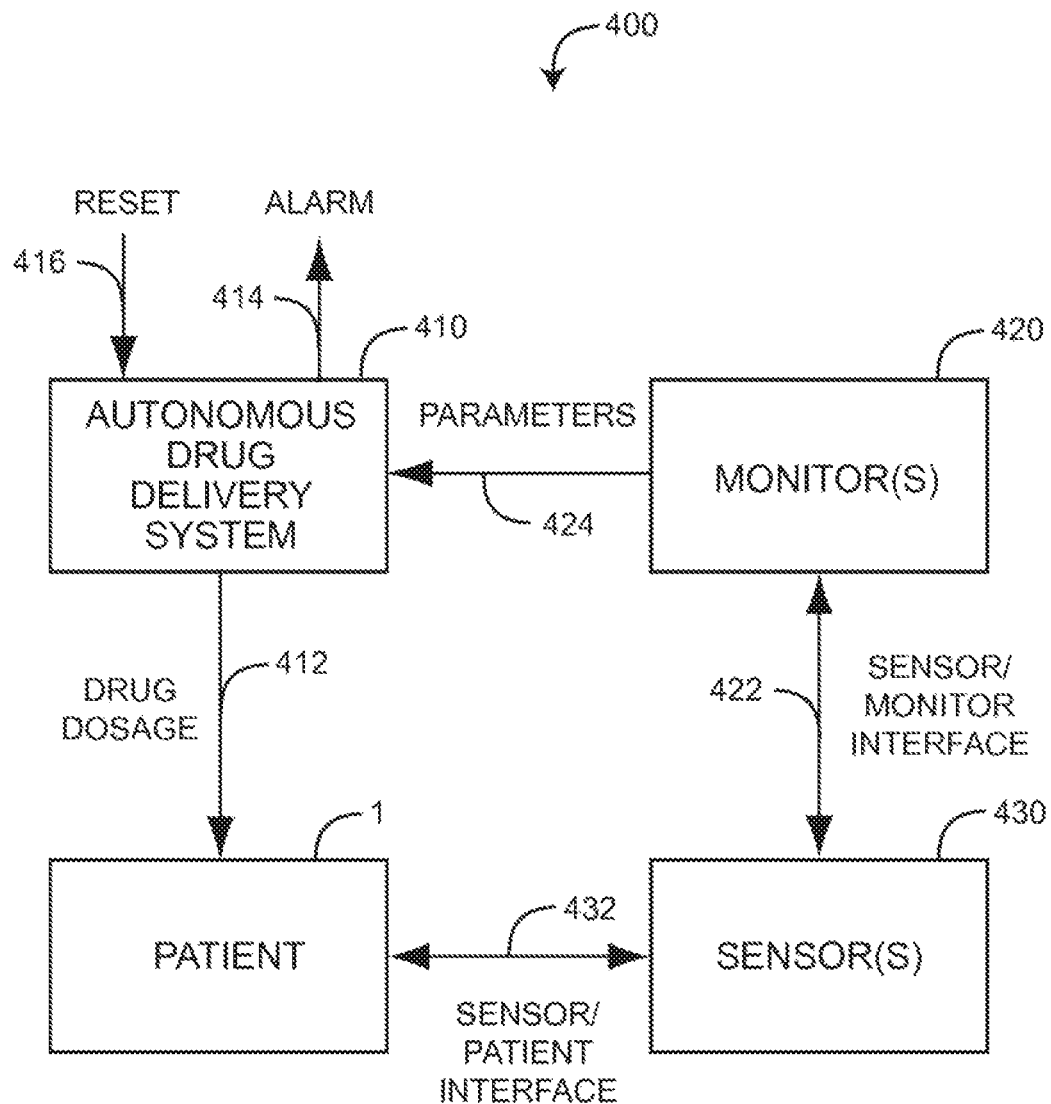
FIG. 4 is a block diagram of an autonomous drug delivery system having fluid connectivity to a patient and electronic communications with sensor(s) and monitor(s)

FIG. 4 illustrates an autonomous drug delivery system 400 having fluid connectivity to a patient 412 and electronic communications 424 with one or more monitors 420. One or more sensors 430 interface 432 with the patient 412, either by direct patient attachment or by remote sensing. For example, an optical sensor 430 may clip to a fingertip site 432 and provide pulsatile blood flow data via cable 422 to a pulse oximeter or blood parameter monitor 420. The pulse oximeter or blood parameter monitor 420 calculates physiological parameters 424, such as oxygen saturation and pulse rate, which are transmitted to the ADDS 410. The ADDS 410 responds to the parameters 424 by regulating (starting, increasing, decreasing or halting) the drug dosage 412 accordingly. The ADDS 410 may generate one or more alarms 414 to alert a caregiver. The caregiver may reset 416 an alarm upon responding to the alert. In an embodiment, communication between the ADDS 410 and a caregiver may be via a wired or wireless network and received at a nurses' station or equivalent.

Figure 5:
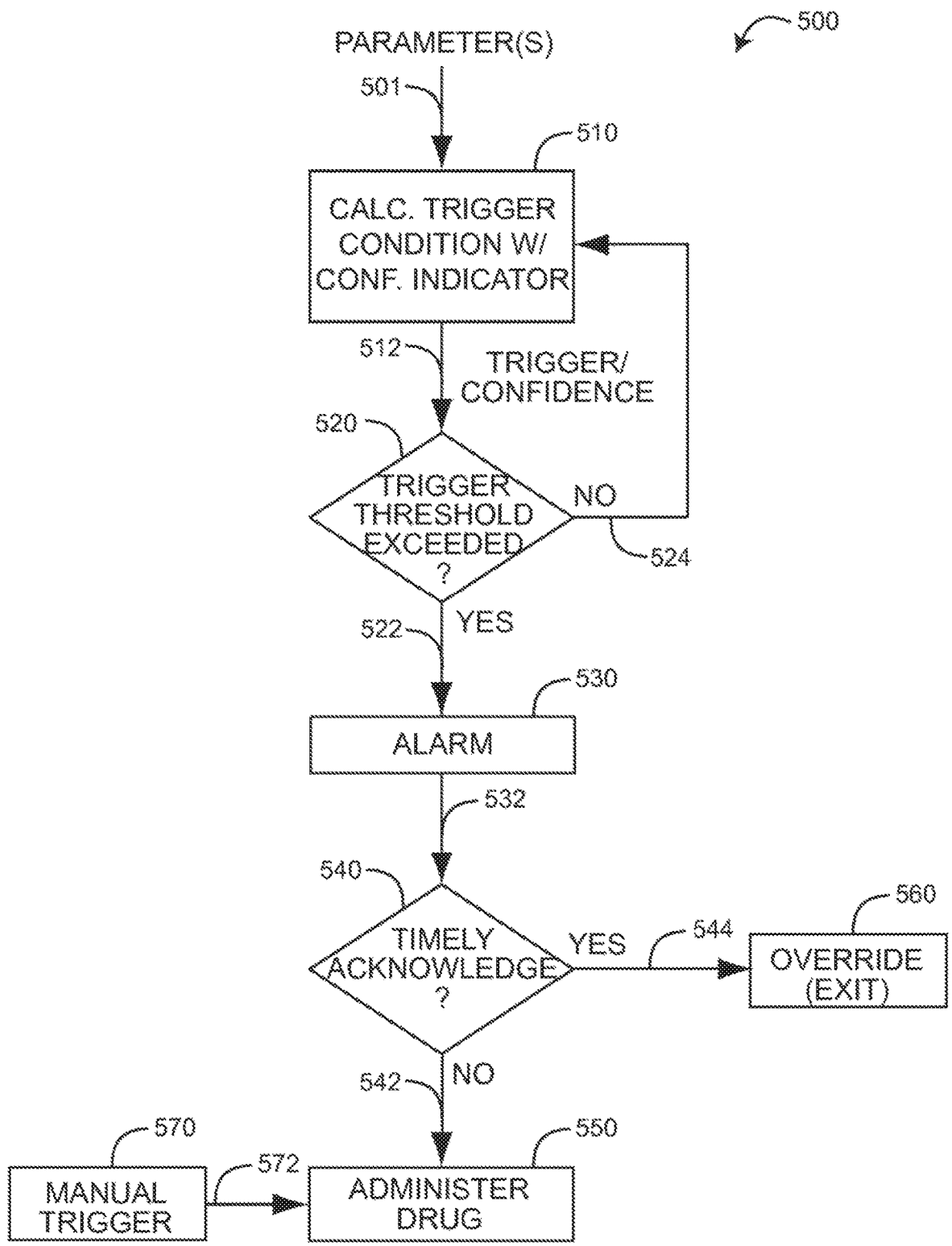
FIG. 5 is a single-rail drug administration decision flow chart.

FIG. 5 illustrates example single-rail drug administration decisions. In this case, there is a single threshold (maximum or minimum) that if exceeded, triggers the ADDS device to administer a rescue drug to a patient. One or more parameters 501 are input to the ADDS device. An ADDS algorithm 510 calculates a trigger condition and an associated confidence indicator 512. If the ADDS trigger threshold is exceeded 520, an alarm 530 is triggered 522. Otherwise 524, ADDS does nothing. If the alarm 532 is timely acknowledged 540, such as by a caregiver pressing an ADDS acknowledge button 544, then ADDS exits 560 and the alarm is silenced. If the alarm 532 is not acknowledged 542, then ADDS administers a rescue drug 550. Note that ADDS has a manual trigger 570 (button press), so as to manual trigger 572 drug administration 550 (see 130 FIG. 1A). In an embodiment, alarms 530 and corresponding acknowledgment times 540 may progress from a local alarm, a network alarm and finally a pager alarm before autonomous drug delivery is triggered.

Figure 6:
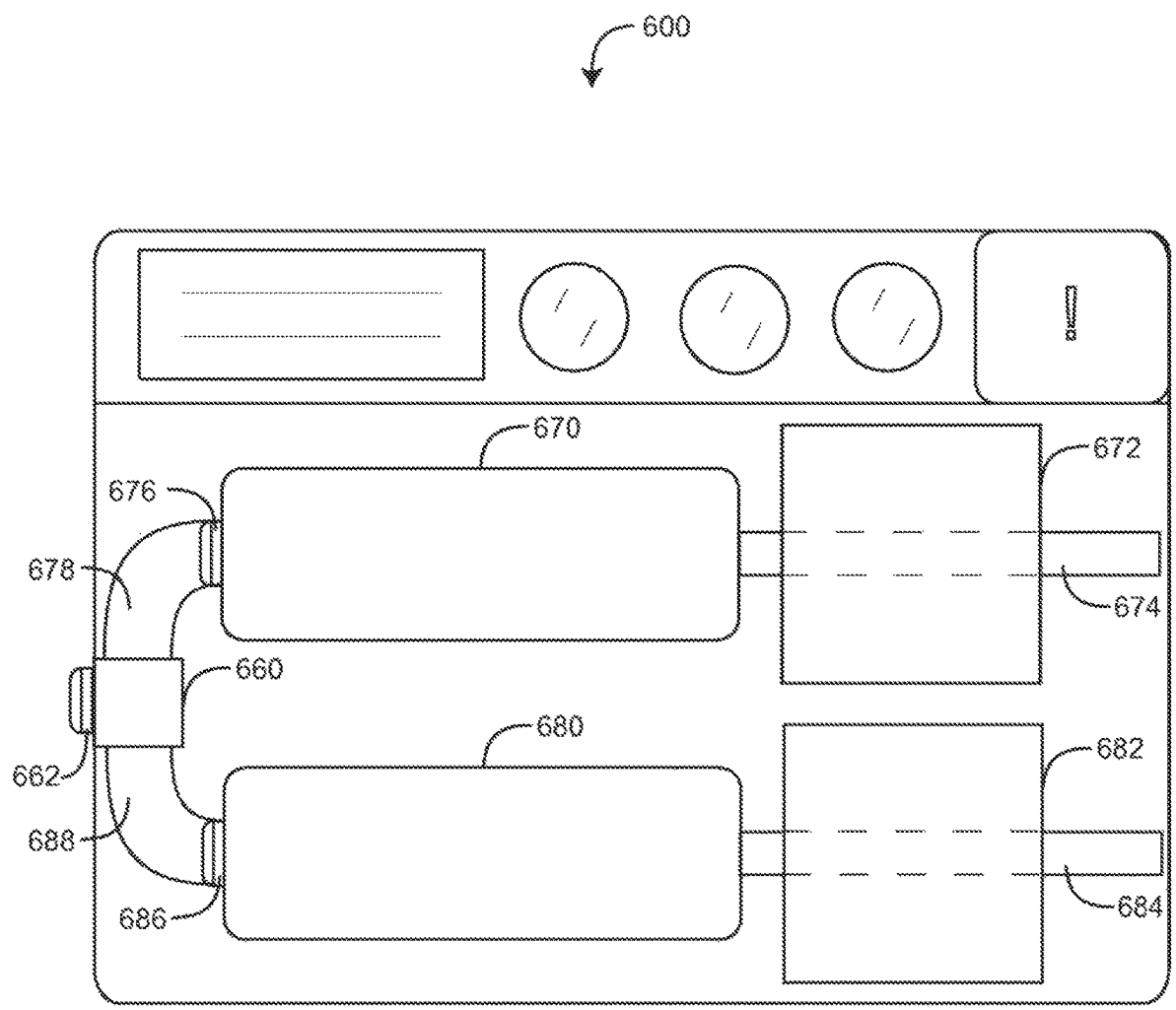
FIG. 6 is a cutaway dual drug reservoir view of an autonomous drug delivery system embodiment.

FIG. 6 illustrates a dual drug reservoir embodiment 600 of an autonomous drug delivery system. A first drug reservoir 670 and a second drug reservoir 680 may each contain the same drug for one or two separate doses or may contain different drugs for different single doses depending on the monitored condition. See, for example FIG. 7. The drug reservoirs 670, 680 share a common nozzle 662. The nozzle 662 has a junction 660 that connects fluid tubes 678, 688 to respect first 676 and second 686 reservoir nozzles. In an embodiment, a clinician has to re-enable the ADDS before a second dose is administered.

Figure 7:
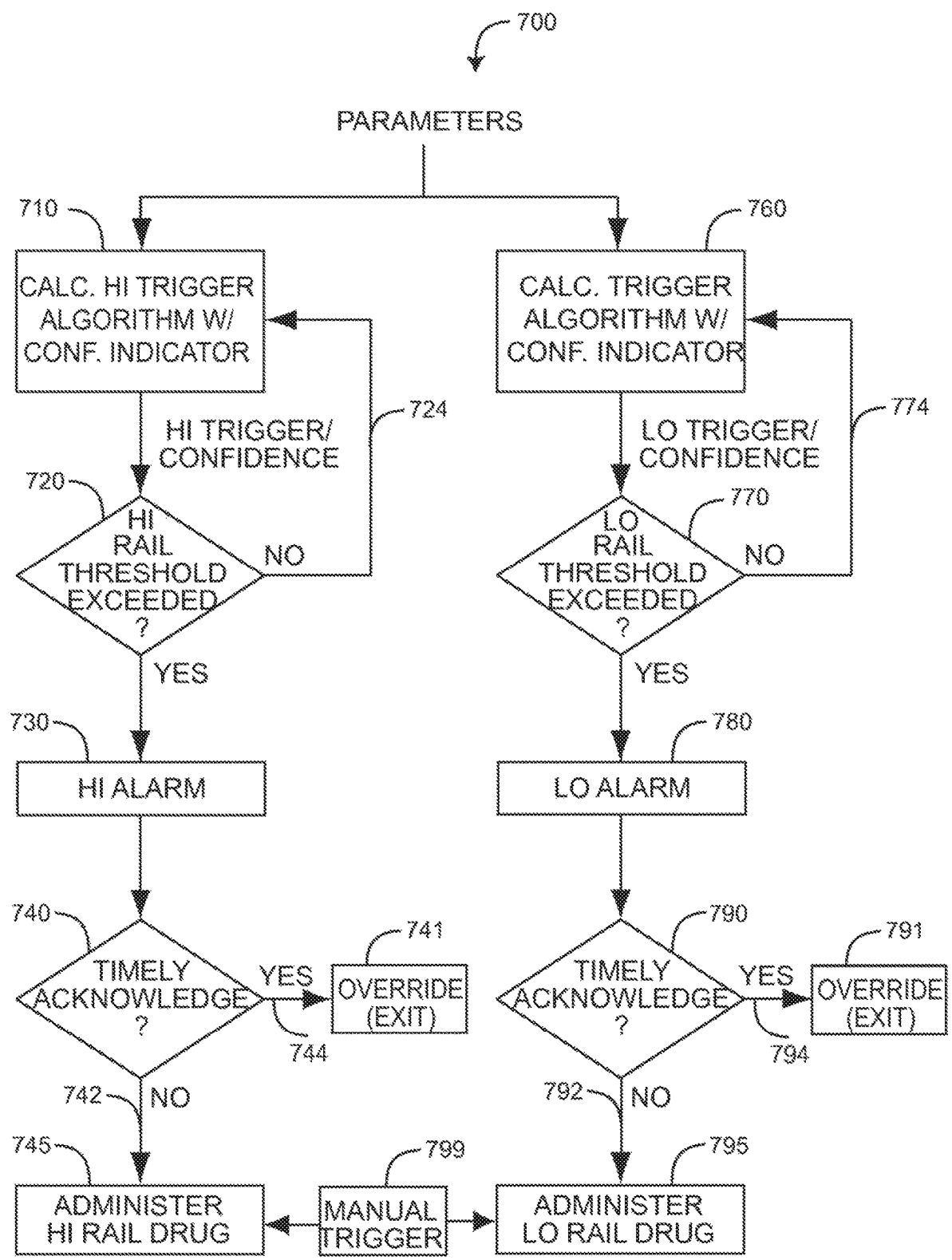
FIG. 7 is a dual-rail drug administration decision flow chart.

FIG. 7 illustrates dual-rail drug administration decisions. In this case, there is a maximum threshold and a minimum threshold. If the maximum threshold is exceeded, for example, one or more parameter values or combinations of parameter values goes over a predetermined limit, then the ADDS device is triggered to administer a rescue drug to a patient. Also, If the minimum threshold is exceeded, for example, one or more parameter values or combinations of parameter values falls below a predetermined limit, then the ADDS device is triggered to administer a rescue drug to a patient. In an embodiment, one rescue drug may be administered upon exceeding the maximum threshold and a different rescue drug many be administered upon exceeding the minimum threshold. One or more parameters 701 are input to the ADDS device. ADDS algorithms 710 and 760 calculate maximum (HI) trigger conditions and minimum (LO) trigger conditions and associated confidence indicator. If either the HI or LO ADDS trigger thresholds are exceeded 720, 770 the corresponding alarm 730, 780 is triggered. Otherwise 724, 774 ADDS does nothing. If a HI or LO alarm 730, 780 is timely acknowledged, such as a caregiver pressing an ADDS acknowledge button 744, 794, then ADDS exits 741, 791 and the alarm is silenced. If the alarm 730, 780 is not acknowledged 742, 792 then ADDS administers the appropriate HI rail 745 or LO rail 795 rescue drug. Note that ADDS has manual triggers 799 (LO or HI button presses), so as to manually trigger either the LO rail drug 745 or the HI rail drug 795.

Figure 8:
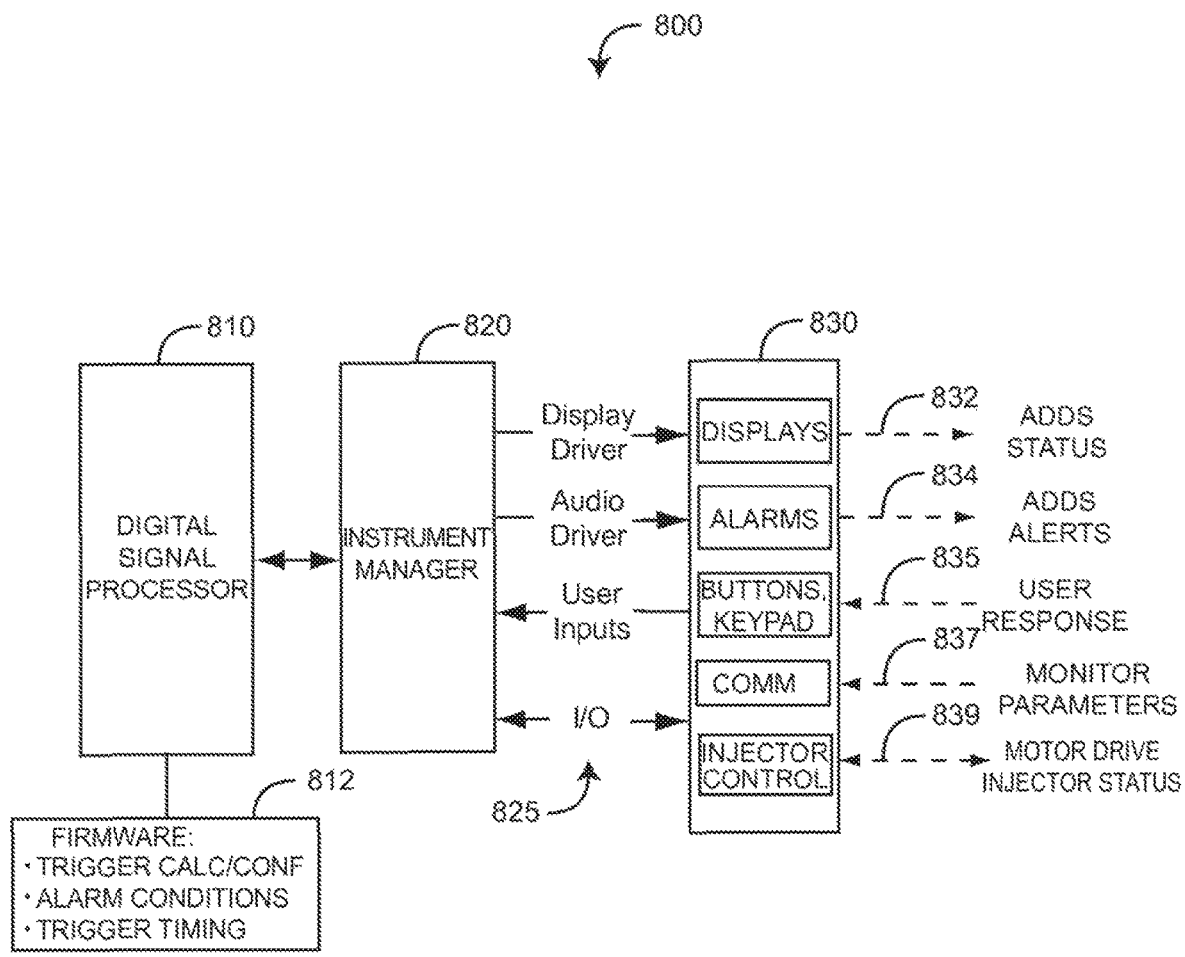
FIG. 8 is a block diagram of an autonomous drug delivery system signal processing and instrument management.

FIG. 8 illustrates an autonomous drug delivery system (ADDS) controller 800 having a digital signal processor (DSP) 810, an instrument manager 820 and interfaces 830. The DSP 810 has algorithms, such as described with respect to FIGS. 5-7, above, for determining trigger conditions, alarms and trigger timing 812. The instrument manager 820 interfaces with the DSP 810 so as to drive the ADDS displays 832 and alarms 834, to receive inputs from the buttons/keypad 835, to communicate with external monitors 837 that derive triggering parameters from patient sensors, to control the injector motor(s) and read injector status 839, such as bolus full/empty and injector active (delivering rescue drug). In an embodiment, DSP firmware records in memory the time and duration of events that triggered drug delivery, including a before and after history of monitor parameters that triggered drug administration.

ADDITIONAL EMBODIMENTS

The following additional embodiments can be implemented together with any of the devices, algorithms, or features described above, in any combination.

Figure 9:
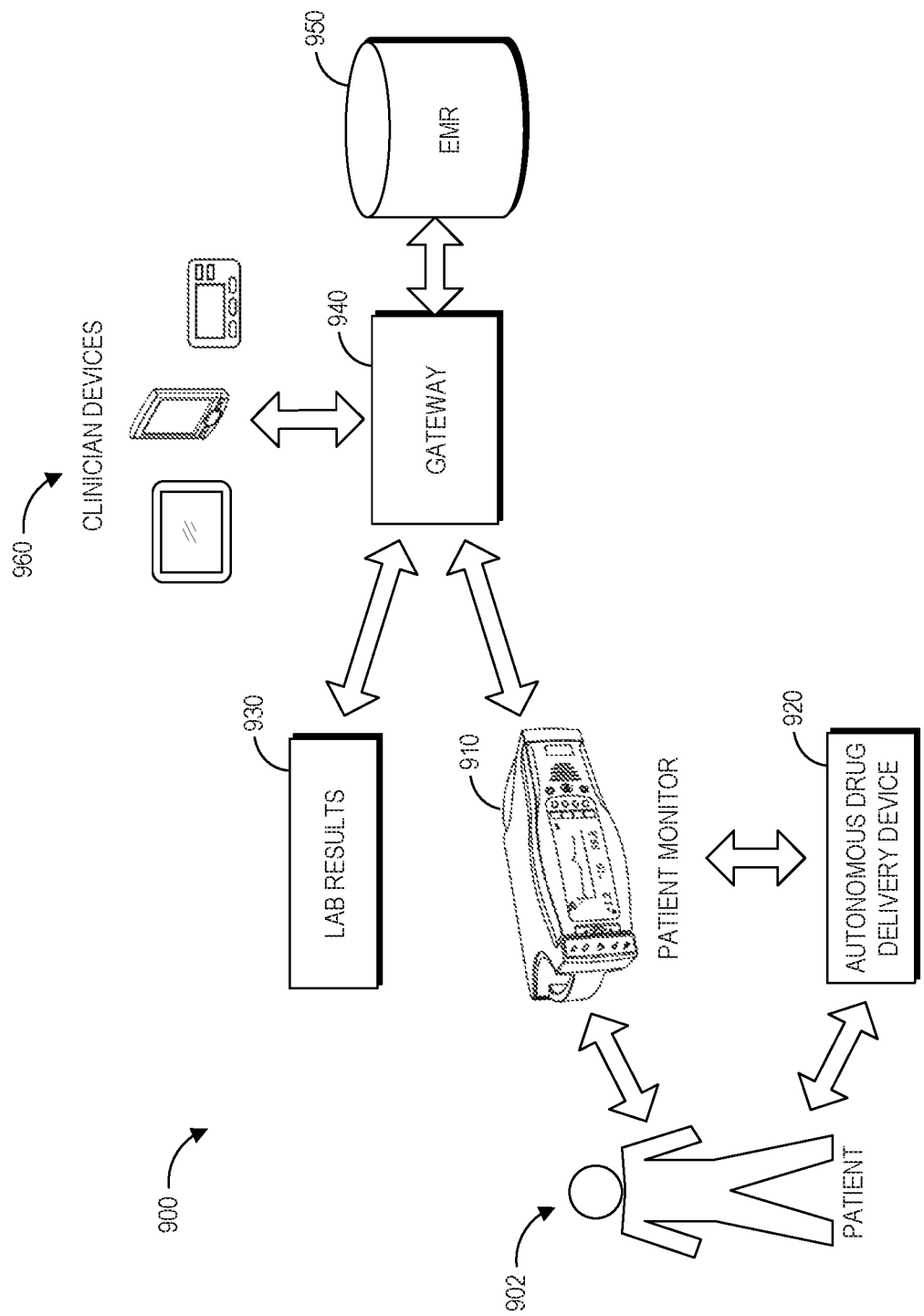
FIG. 9 is a block diagram of an example automated first responder system.

FIG. 9 depicts an example automated first responder system 900. In the automated first responder system 900, a patient 902 is shown in communication with a patient monitor 910 and an autonomous drug delivery device 920. For instance, the patient monitor 910 may be in wireless or electrical communication with one or more sensors coupled with the patient. Examples of such sensors are described above, and may include, for example, optical sensors, acoustic respiratory sensors, ECG sensors, brainwave measurement sensors, blood pressure sensors, and the like.

The patient monitor 910 and the autonomous drug delivery device 920 can have some or all of the features of similar devices described above. For instance, the patient monitor 910 can include any of the controller features described above with respect to FIG. 8. In general, the patient monitor 910 may include one or more hardware processors, memory, and a display. Alternatively, the display may be optional, and the patient monitor 910 can output patient data to a separate display. Likewise, the autonomous drug delivery device 920 can have some or all the features of the ADDS embodiments described above.

The patient monitor 910 is shown in communication with a gateway device 940. The patient monitor 910 may communicate with the gateway device 940 wired or wirelessly over a hospital network (not shown). The hospital network may include a local area network, a wide area network, an intranet, the Internet, combinations of the same, or the like. The gateway device 940 can facilitate communication across the network between multiple devices shown in the system 900. These devices can include clinician devices 960, which may include tablets, pagers, smart phones, laptops, computers, nurses' station computers, and the like. In addition, the gateway 940 is shown in communication with an electronic medical record (EMR) database 950, which can store lab results 930 obtained from laboratory tests applied to the patient 902. The patient monitor 910 may access the EMR 950 through the gateway 940 to obtain access to the lab results 930 as well as other data, including data regarding charting of the patient's conditions, medications, tests, and the like applied during a hospital stay. Of course, the system 900 can also be applied in any clinical setting, and not just in a hospital. However, for convenience, this specification refers specifically to hospital embodiments, without loss of generality.

The automated first responder system 900 can implement any of the features described above with respect to FIGS. 1-8. In addition, in certain embodiments, the automated first responder system 900 can also implement the additional features discussed below. For instance, the patient monitor 910 can initiate treatment workflows automatically based on an analysis of patient data. The patient data can include data measured from physiological sensors, as well as data obtained from lab results and the like. Using this patient data, the patient monitor 910 can determine whether the data corresponds with or matches any diagnostic model or models stored in physical computer storage. A diagnostic model can be represented as a data structure or the like and can relate a set of patient data inputs to a possible diagnosis and to a treatment workflow to address the possible diagnosis. Example treatment workflows are described below with respect to FIG. 11.

If the patient data matches a diagnostic model (examples of which are described below), the patient monitor 910 can initiate a treatment workflow automatically to begin treatment of the patient. The treatment workflow can include administration of a substance, such as a drug, using any of the techniques described above. The treatment workflow can also include other actions, such as ordering lab tests, alerting clinicians, and the like.

As part of a treatment workflow, the patient monitor 910 may communicate an instruction or signal to the autonomous drug delivery device 920 to cause the autonomous drug delivery device 920 to supply a dose or bolus of medication to the patient 902. In one embodiment, the autonomous drug delivery device 920 is an intravenous therapy device, such as an intravenous (IV) drip device. Thus, the autonomous drug delivery device 920 may administer substances other than drugs to the patient 902, such as saline solution. In some embodiments, a saline solution may be combined with a drug to be administered to the patient 902.

As another example aspect of a treatment workflow, the treatment workflow may include initially administering a first dosage of a substance to a patient without requiring initiation by a clinician. Optionally, however, the patient monitor 910 may produce an output (for example, on the display) that provides the clinician with an option to intervene and stop administration of a substance or stop any other aspect of a treatment workflow.

Later, if the patient data again matches the diagnostic model, such that an additional administration of a substance may be warranted, the treatment workflow may include alerting a clinician instead of administrating the second dosage. In this manner, it is possible to administer a relatively harmless or low dosage of a substance first to the patient without human intervention in order to provide an automated first response but subsequently to involve a clinician to avoid accidentally overdosing the patient with the substance.

As another example, the patient monitor 910, upon detecting that a diagnostic model has been matched, can alert a clinician who may be remote from the patient of the patient's potential condition. The clinician can then respond to the alert in various ways, discussed below.

The alert to the clinician may be sent as a message over a network, such as the hospital network, to a clinician's device (such as a smartphone, tablet, laptop, desktop, or other computing device). The alert may be sent as an electronic mail message, a text message, or as another type of message, including a custom message for a custom mobile application or web application installed or accessed on the clinician's device. The alert can include any subset of the following information: patient identifying and/or demographic information, the patient data or a summary thereof (such as waveform(s) and/or physiological parameter value(s)), an indication of the patient's condition such as an indication that a specific diagnostic model has been met (such as "this patient may have sepsis" or "possible opioid overdose detected"), and a recommended treatment course (such as a recommendation to administer a bolus of medication, order a lab test, or any other aspect of a workflow discussed herein).

Upon receipt of the alert, software on the clinician's device can output the message to the clinician optionally with functionality for the clinician to respond. For instance, the clinician's device may have a mobile application or browser installed that can receive the alert and output a user interface with the alert for presentation to the clinician. The user interface may include buttons, input fields, or other user interface controls that allow the clinician to interact with the alert. For instance, the user interface may provide functionality for the clinician to accept or adjust the recommended treatment. Should the clinician accept the recommended treatment, the software on the clinician's device can transmit the acceptance to the patient monitor 910, which can cause the autonomous drug delivery device 920 to deliver the recommended dosage to the patient (or order a lab or perform another workflow action). Should the clinician adjust the recommended treatment, this adjustment may be communicated to the patient monitor 910, which can cause the autonomous drug delivery device 920 to deliver the adjusted dosage to the patient (or order a lab or perform another workflow action).

Likewise, the clinician can remotely create or adjust a treatment workflow, whether lab order or drug administration or other workflow, and can cause this adjustment to be sent to the patient monitor 910 for application to the patient. For example, the clinician may receive patient data with or without a recommendation for treatment. The clinician can then access a user interface on the clinician's device to input a desired treatment or workflow, even if one was not recommended by the patient monitor 910. The clinician device can transmit this selected treatment or workflow to the patient monitor 910. If the treatment or workflow includes the administration of a drug, the patient monitor 910 can cause the autonomous drug delivery device 920 to deliver the selected dosage to the patient. Any of the autonomous drug delivery devices described herein can include a plurality of different intervention medications ready to be injected or supplied to the patient intravenously as desired.

Figure 10:
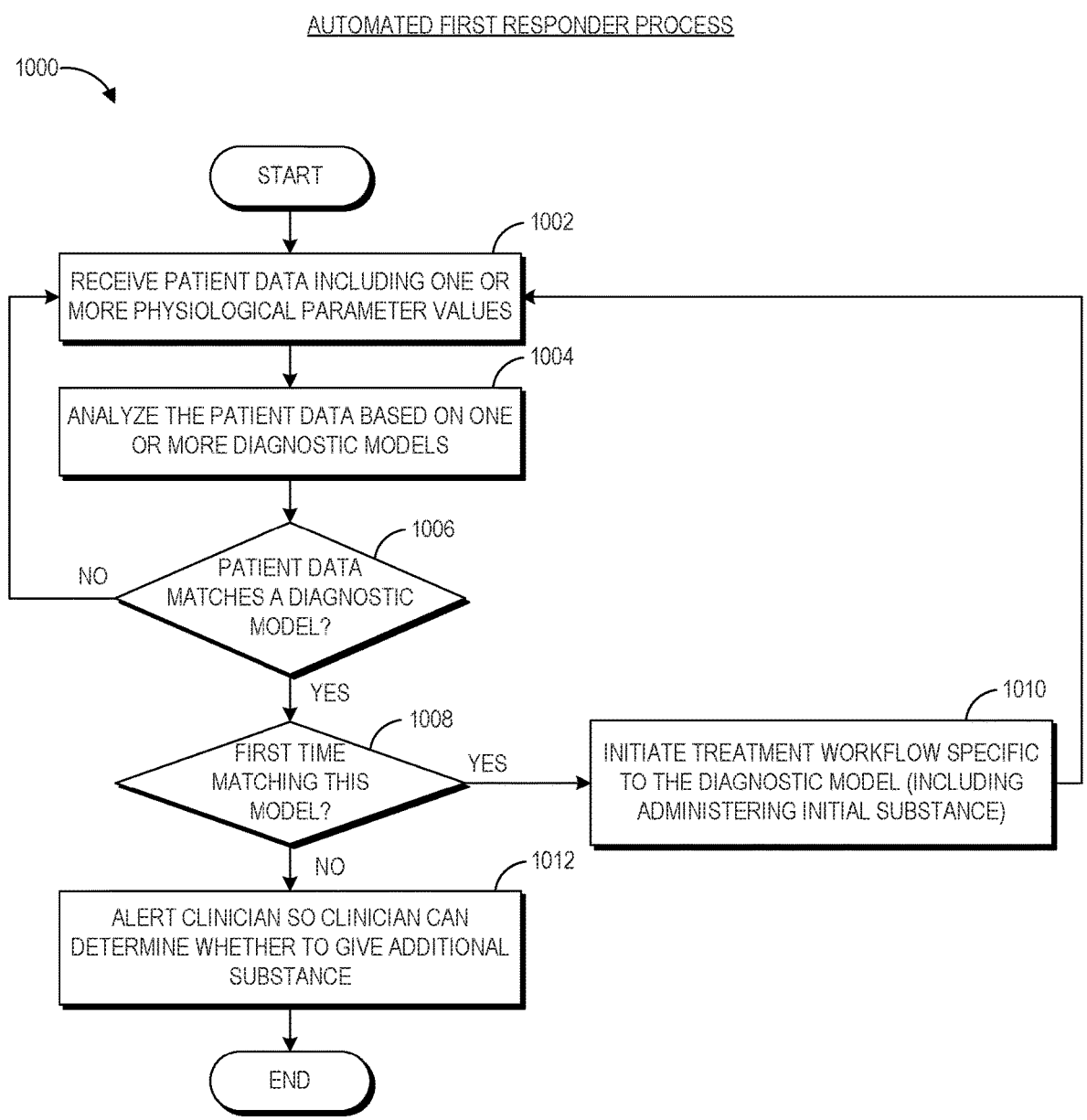
FIG. 10 is a block diagram of an example automated first responder process.

FIG. 10 depicts an example automated first responder process 1000. The automated first responder process 1000 can be implemented by any of the systems described above. For instance, the patient monitor 910 can implement the process 1000. In another embodiment, however, at least part of the process 1000 can be implemented in any server, for instance, in a cloud computing environment. For example, the process 1000 can be implemented in a server that receives information from the patient monitor 910, and which provides outputs to the monitor 910 to enable the monitor 910 to perform portions of a treatment workflow (such as initiate delivery of substance by the autonomous drug delivery device 920). For ease of description, however, the process 1000 is described as being implemented primarily by the patient monitor 910.

At block 1002, the patient monitor 910 receives patient data including one or more physiological parameter values. The one or more physiological parameter values may include values of one or more physiological parameters, such as respiration rate, oxygen saturation, blood pressure, heart rate, and the like (as well as any other parameters discussed above). In addition to receiving one or more physiological parameter values, the patient monitor may receive additional patient data, such as lab test values. One example of a lab test value that may be useful is white blood cell count (WBC). More generally, any blood test value, urine test value, stool test value, or any other lab test value may be used.

At block 1004, the patient monitor 910 analyzes patient data based on one or more diagnostic models. For example, the patient monitor 910 can compare the patient data to any diagnostic models stored in memory or other physical computer storage. The diagnostic models may include one or more criteria for determining whether to initiate a treatment workflow. Evaluating this criteria can involve performing a comparison of the patient data with specific values, thresholds, trends, changes, combinations, ratios, and the like. A specific combination of parameter trends, for instance, may indicate that a patient is likely experiencing an opioid overdose, sepsis, hypovolemia, or any of a number of other conditions. Specific examples of diagnostic models are presented below with respect to FIG. 11.

At block 1006, the patient monitor 910 determines whether the patient data matches a diagnostic model. If not, the process 1000 loops back to block 1002, and the patient monitor 910 continues to receive patient data. If the patient monitor 910 identifies a match in a diagnostic model, however, the process 1000 proceeds to block 1008, where the patient monitor 910 determines whether this is the first time that the patient data matches this model. If so, at block 1010 the patient monitor 910 initiates a treatment workflow specific to the diagnostic model. The process 1000 then loops back to block 1002.

Diagnostic models can be represented as data structures or data definitions stored in physical computer storage or memory. Diagnostic models can also be generated empirically by collecting data from a plurality of patients, measuring the same or similar physiological parameters, and by analyzing patient treatments and subsequent outcomes. Diagnostic models can also be rule-based models, or a combination of empirical and rule-based models. Some example rule-based models are described below with respect to FIG. 11.

In some embodiments, at block 1006, the patient monitor 910 calculates a confidence value that represents a likelihood that the patient data matches the diagnostic model. The confidence value can be a percentage value, a score on any scale, or the like. The patient monitor 910 can calculate a higher confidence value based on the patient data more closely matching the diagnostic model or a lower confidence value based on the patient data less closely matching the diagnostic model.

The confidence value can also be based determined at least in part on parameter value confidence. For instance, the patient monitor 910 can calculate a confidence value for a parameter value, indicating a likelihood of the parameter value being accurate. The confidence value for matching the diagnostic model can therefore take into account parameter confidence values. For example, if two parameters are analyzed with respect to a diagnostic model, and the two parameters have a calculated confidence of 95% and 75% respectively, the patient monitor 910 can calculate a confidence value that is the mean of these two values (85%) or some other combination of these two values (such as selecting the lower confidence value as the overall confidence value). Then, the patient monitor 910 can compare the two parameter values with the diagnostic model and determine how closely the parameters match the model. If the parameters match the model well, the patient monitor 910 can give a high confidence score, but the patient monitor 910 may then modify this high confidence score based on the parameter value confidence scores. For instance, if the confidence value for matching the model is 95%, but the parameter value confidence is 75%, the patient monitor 910 may lower the confidence for matching the model (e.g., by multiplying the two numbers to reach ~71%). Many other ways for calculating confidence are possible.

The patient monitor 910 can determine that if the confidence value is too low, that the diagnostic model is not met. Alternatively, the patient monitor 910 can determine that the diagnostic model is met even when a confidence value is low but may output an indication of the confidence value (for example, on a display) so that a clinician can determine whether to trust the diagnostic model match. The patient monitor 910 can output an indication of the confidence value regardless of the value, whether it be high or low. The indication can be the value itself or some representation of that value, such as a graphic representation (for example, a bar with a size corresponding to the confidence value).

However, if at block 1008 it is not the first time that the patient data matches this model, then at block 1012 the patient monitor 910 alerts a clinician so that the clinician can determine whether to give an additional substance or perform an additional action associated with the treatment workflow. The patient monitor 910 can alert the clinician by outputting the alert or alarm audibly and/or visually. The patient monitor 910 can also alert the clinician by transmitting an alert or alarm message to the clinician over a network, such as a hospital network, a local area network (LAN), a wide area network (WAN), the Internet, an Intranet, or the like.

Thus, the process 1000 can provide an automated treatment of the patient as a first response and defer clinician intervention until a subsequent response. For instance, a first time when it is determined that the patient data indicates a possible opioid overdose, the patient monitor can cause an initial dosage of an overdose-treating medication like Narcan to be supplied to the patient. However, if later the patient data again indicates that the patient is suffering from a possible overdose, the patient monitor 910 can alert a clinician to determine whether the patient needs an additional dose.

In an embodiment, if the clinician does not respond rapidly enough (for example, with in a predetermined time period), the patient monitor 910 can automatically supply a second dose to the patient. The patient monitor 910 may be restricted from supplying a second dose to the patient unless the patient data includes a life-threatening parameter value or values (such as a very low pulse rate, oxygen saturation value, or blood pressure). More generally, the patient monitor 910 can take into account any of the following variables when determining whether to administer a subsequent dose of a drug to a patient, among others: time elapsed since an alarm without a clinician disabling the alarm or otherwise responding to the alarm; severity of the patient data; amount of the earlier and/or subsequent dosage (a lower dose may be less harmful, and thus subsequent low doses might be permitted without clinician intervention); the type of drug administered (some drugs may have less risk for administering subsequent doses than others); specific facts about the patient including demographics, comorbidities, or the like (for example, a neonate might be at higher risk than an adult for a subsequent dose, or a patient with a certain disease might be at a higher risk than patients without that disease for a certain dose); other medications taken by the patient (a subsequent dose might be potentially more harmful if a patient is taking other medication that can react adversely upon a subsequent dose); prior permission by a clinician (the patient monitor 910 can output a user interface that enables a clinician to explicitly give permission for one or more subsequent automatic administration of doses when needed); combinations of the same, or the like.

Figure 11:
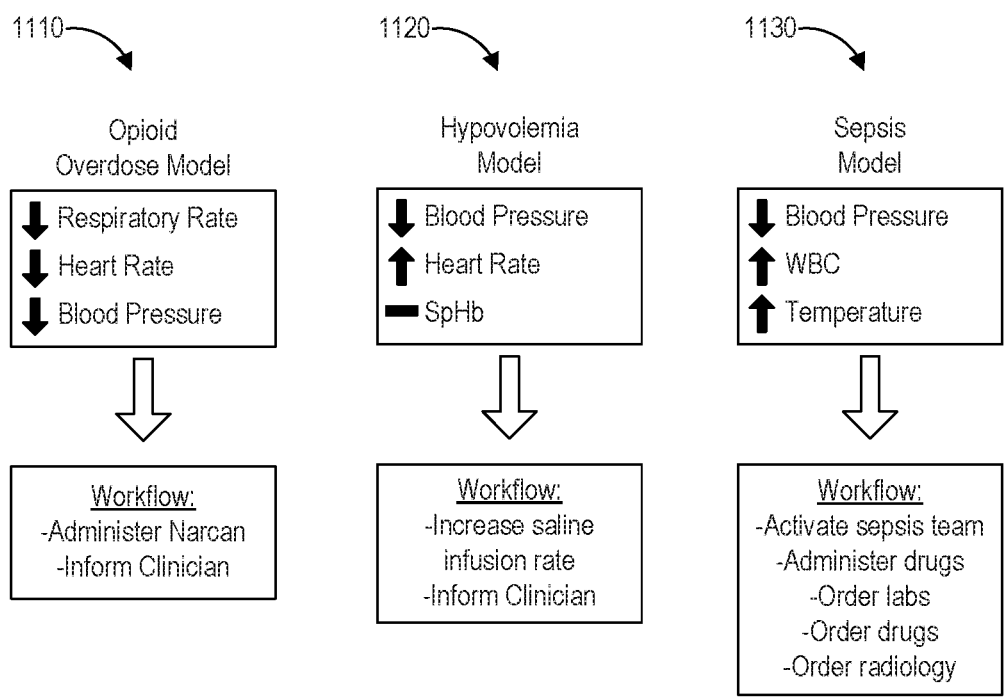
FIG. 11 is a block diagram of example diagnostic models.

FIG. 11 depicts example diagnostic models 1110, 1120, and 1130. These diagnostic models show example criteria corresponding to possible diagnoses and associated example treatment workflows. The first model 1110 is an opioid overdose model. In this model, if respiratory rate, heart rate, and blood pressure have decreased (for example, are trending downward or pass below a threshold), then these parameter changes may indicate an opioid overdose and may trigger a treatment workflow. A decrease in temperature can also be indicative of opioid overdose in the model. The example treatment workflow shown includes an administration of Narcan and informing a clinician. Informing a clinician may include sending an alert or alarm to clinician as described above, recording an indication in the patient's chart (such as in the EMR), combinations of the same or the like. The treatment workflow shown may be modified to include more or fewer steps. In addition, the steps of the treatment workflow and other treatment workflows described herein may be implemented in any order.

The second model 1120 is a hypovolemia model. In this model 1120, if blood pressure has decreased (for example, trending downward or below a threshold), heart rate is increased (for example, trending upward or above a threshold), and hemoglobin level (whether measured noninvasively (SpHb) or in a lab (THb)) is steady (for example, no positive or negative trend, or slope of the average trend is within a tolerance, or the parameter value has not changed more than a threshold amount for a period of time), this may be an indication that the patient is suffering from hypovolemia. The treatment workflow that may be triggered may include increasing a saline infusion rate (to increase blood volume and/or sodium levels in the blood), supplying oxygen (not shown; can increase the efficiency of the patient's remaining blood supply), and informing a clinician (similar to above). Although not shown, other steps may be included in these and other treatment workflows, such as ordering other drugs, recommending possible surgery (for example, to stop internal bleeding for some hypovolemic patients), and so on.

The third model 1130 shown is a sepsis model. In this model, if blood pressure is down, white blood cell count is up, and temperature is up (for example, indicating a fever or conversely, too low temperature), the patient may be suffering from sepsis. Increased heart rate (for example, above a threshold), increased respiratory rate (for example, above a threshold), and decreased systolic blood pressure (for example, below a threshold) are other example factors that may be included in the model. The example treatment workflow shown includes activating a sepsis team (for example, informing a team of clinicians having different tasks that can assist with treating sepsis), administering drugs, and ordering labs, drugs, and radiology tests. The treatment workflow can also include automatically administering intravenous fluids and/or antibiotics. The treatment workflow can also include recommending transfer of the patient to an intensive care unit (ICU).

As stated above, there are many other diagnostic models that may be employed by the patient monitor to initiate treatment workflow. Any of the models may be combined or modified by other criteria. For instance, administration of some drugs can cause side effects, which may be detected or inferred from the patient data. As an example, administration of some drugs can impact blood pressure negatively. Detecting a change in blood pressure after a drug has been administered may cause a treatment workflow to begin that stops administration of the drug (if being administered automatically) or that recommends to a clinician to consider stopping administration of the drug.

As another example, a diagnostic model may be provided for detecting bedsore formation (or risk factors for bedsore formation). This diagnostic model may take input from a pressure mat on the patient's bed or on the floor next to the bed, which can provide an electrical signal output when a patient moves or steps on the mat. Lack of movement or lack of stepping on a mat may indicate that the patient is not moving enough and is therefore susceptible to a bedsore. A possible treatment workflow may be executed, including alerting a caregiver that the patient should be moved in some manner to attempt to prevent bedsore formation.

Diagnostic models may also take into account more than the physiological parameters and lab tests described herein as examples of patient data. Additional patient data may be relevant to evaluating whether a particular model is applicable. For instance, data regarding the patient's gender, age, or other comorbidities may impact whether or not the patient monitor determines that a particular diagnostic model is applicable. Likewise, any of these factors may be used to modify a treatment workflow when a diagnostic model is indicated as being applicable. For example, if a patient is indicated as being a smoker (which may be a data point stored in the EMR record for that patient), a treatment workflow that involves applying ventilation from a ventilator may include supplying more carbon dioxide than would be supplied to a non-smoking patient because the smoker's lungs are adapted to higher carbon dioxide levels when breathing.

In another embodiment, a previous or current treatment may be an input into a diagnostic model as part of the patient data. Thus, a previous or current treatment may affect whether a diagnostic model is applied and/or how a treatment workflow is executed. For instance, if the patient has just had hip replacement surgery (which may be a data point stored in the EMR record for that patient), the patient monitor may be on heightened alert to search for indications of sepsis. The patient monitor may therefore be more sensitive to changes in blood pressure, temperature, and white blood cell count to determine whether sepsis is occurring. More specifically, a lower change in blood pressure, white blood cell count, or temperature than for other patients not having had hip replacement recently may be applied to trigger a sepsis treatment workflow.

Moreover, as seen in the example workflow shown in FIG. 11, the level of alert provided to a clinician may vary depending on the seriousness of the diagnostic model detected. With sepsis, for instance, an entire team may be alerted, whereas with other conditions, like hypovolemia, a single clinician may be alerted. Of course, the number of clinicians alerted for any given condition can depend on the severity of that condition, the severity of the physiological parameter values, and so on, and may deviate from that shown in FIG. 11.

Patient data in any of the models described herein can be analyzed according to a variety of different types of threshold values. Two general types of thresholds may be used—static thresholds and dynamic thresholds. Static thresholds can include predetermined thresholds that are the same for a class of patients, such as the same set of thresholds for all adults or a different set of thresholds for all neonates. Dynamic thresholds can include thresholds that are based on the current patient's mean or baseline physiological parameter values. Table 1 below depicts example static thresholds and dynamic thresholds for adult patients for some physiological parameters:

TABLE 1

Example Adult Parameter Threshold Values

| Physiological Parameter | Static Threshold | Dynamic Threshold |
|---|---|---|
| Low Respiratory Rate | ≤6 RPM | >2 SD from individual mean |
| Low Heart Rate | ≤35 BPM | >2 SD from individual mean |
| Low Blood Pressure (MAP) | ≤63 mmHg | >2 SD from individual mean |
| Increased Heart Rate | ≥90 BPM | >2 SD from individual mean |
| Increased WBC | ≥12,000/uL | >2 SD from individual mean |
| Increased Temperature | ≥38.3 degrees C. | >2 SD from individual mean |

In Table 1, "SD" refers to "standard deviation," "MAP" refers to mean arterial pressure, "RPM" refers to respirations or breaths per minute; and "BPM" refers to beats per minute.

The static threshold category may be further subdivided into two subcategories—critical thresholds and normal thresholds. Critical thresholds may represent thresholds below (or above) which a physiological parameter is at a critical or life-threatening value. Normal thresholds can represent less-critical or less life threatening values that still nevertheless may be indicative of a diagnosis per a diagnostic model. Some diagnostic models can use critical thresholds, while others may use normal thresholds. Some diagnostic models may use a critical threshold for one parameter and a normal threshold for another parameter.

The patient monitor can evaluate static thresholds or dynamic thresholds to determine whether a diagnostic model is met. In addition, the patient monitor can evaluate both static and dynamic thresholds to determine whether a diagnostic model is met. For instance, the patient monitor can perform a logical "OR" operation based on a comparison of physiological models to both static and dynamic thresholds. To illustrate one example implementation, if a patient's heart rate satisfies either a static or a dynamic threshold (or both), then the patient monitor can determine that the patient's heart rate satisfies a heart rate portion of a diagnostic model. In another embodiment, the patient monitor performs a logical "AND" operation (or some other logical operation) based on a comparison of physiological models to both static and dynamic thresholds.

In an implementation, the patient monitor can rely on static thresholds early in a patient's hospital stay, where mean or baseline values of the patient's parameters are unknown or less reliable to calculate based on lack of patient data. Later in the patient's hospital stay (possibly even some minutes or hours after admission), the patient monitor can rely on dynamic thresholds after enough data about the patient is available to determine mean or baseline values.

Figure 12:
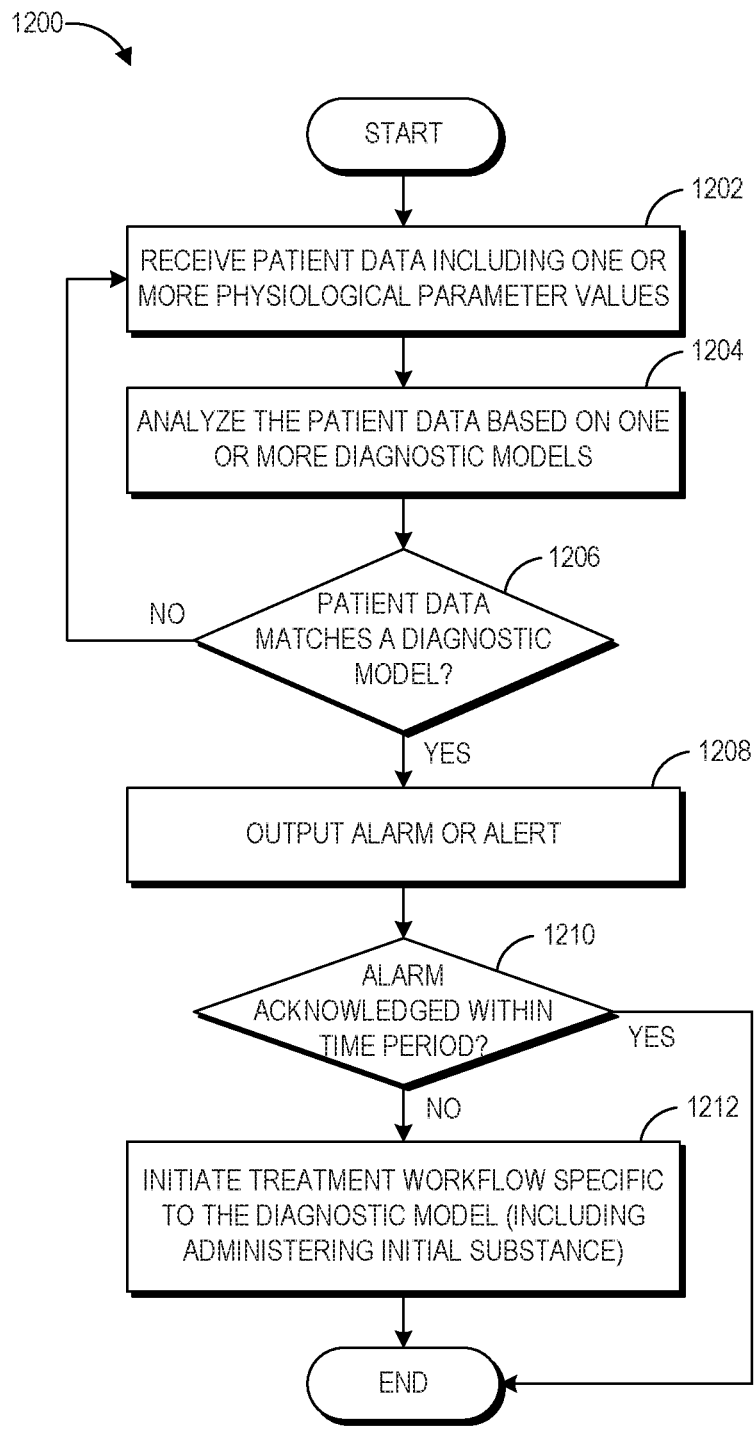
FIG. 12 is a block diagram of another example automated first responder process.

FIG. 12 depicts another example automated first responder process 1200. The automated first responder process 1200 can be implemented by any of the systems described above. For instance, the patient monitor 910 can implement the process 1200. In another embodiment, however, at least part of the process 1200 can be implemented in a server, for instance, in a cloud computing environment. The process 1200 can optionally be implemented in a server that receives information from the patient monitor 910, and which provides outputs to the monitor 910, to enable the monitor 910 to perform portions of a treatment workflow. For ease of description, however, the process 1200 is described as being implemented primarily by the patient monitor 910.

Blocks 1202 through 1206 can proceed the same or similar to blocks 1002 through 1006 of the process 1000 (see FIG. 10). At block 1208, if the patient data matched a diagnostic model in block 1206, the patient monitor 910 outputs an alarm or alert to a clinician. This alarm or alert can be provided in a similar manner to the alarm or alert output in block 1012 of the process 1000 (see FIG. 10). However, in this process 1200, the patient monitor 910 determines at block 1210 whether the alarm (or alert) has been acknowledged within a predetermined time period (such as 30 seconds, 1 minute, 2 minutes, or some other time period). For instance, the patient monitor 910 can determine whether a clinician disabled the alarm as an indication that the alarm was acknowledged. Disabling of the alarm can indicate that the clinician visited the patient's bedside and explored the situation that led to the alarm.

If the alarm was acknowledged within the predetermined time period, the process 1200 can end. If the alarm was not acknowledged within the predetermined time period, then at block 1212, the patient monitor 910 can initiate a treatment workflow specific to the diagnostic model, as explained above with respect to block 1010 of FIG. 10.

This process 1200 therefore enables the patient to receive some form of medical attention, such as specified by a treatment workflow, if a clinician is unable to treat the patient within a certain amount of time. This process 1200 can save lives and increase patient comfort in busy hospitals or in other triage situations.

Of course, should the patient data again match a diagnostic model, the patient monitor 910 can implement blocks 1008 and 1012 of the process 1000 or the like.

CONCLUSION

An autonomous drug delivery system and an automated first responder system have been disclosed in detail in connection with various embodiments. These embodiments are disclosed by way of example only and are not to limit the scope of this disclosure or the claims that follow. One of ordinary skill in art will appreciate many variations and modifications. For instance, many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor comprising digital logic circuitry, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. An automated first responder method, the method comprising:
   under control of a hardware processor,
   receiving patient data comprising a plurality of physiological parameter values, at least some of the physiological parameter values derived from physiological signals obtained from one or more physiological sensors coupled with a patient;
   analyzing the patient data to determine whether the patient data matches at least one of a plurality of diagnostic models represented in computer memory, each diagnostic model representing a possible diagnoses of a different condition and resulting in administration of a different drug;
   determining that the patient data matches the at least one diagnostic model;
   responsive to said determining, initiating a treatment workflow comprising automatically administering a substance to the patient based, at least in part, on the at least one diagnostic model;
   subsequent to said administering, analyzing the patient data again and determining that the patient data again matches the at least one diagnostic model; and
   responsive to said determining that the patient data again matches the at least one diagnostic model, sending an alert to a clinician over a hospital network, the alert indicating a recommendation that the clinician provide an additional amount of the substance but not automatically providing the additional amount of the substance.

2. The method of claim 1, wherein said receiving the patient data further comprises receiving lab data.

3. The method of claim 2, wherein the lab data comprises data representing a white blood cell count.

4. The method of claim 1, wherein said analyzing the patient data comprises identifying a trend in the physiological parameter values and determining whether the trend corresponds with predetermined trends in the at least one diagnostic model.

5. The method of claim 1, wherein said determining that the patient data matches the at least one diagnostic model comprises identifying a decrease in one of the physiological parameter values and an increase in another one of the physiological parameter values.

6. The method of claim 1, wherein the at least one diagnostic model represents one of the following: an opioid overdose diagnostic model, a hypovolemia diagnostic model, or a sepsis diagnostic model.

7. The method of claim 6, wherein the opioid overdose diagnostic model corresponds to a decrease in respiratory rate, a decrease in heart rate, and a decrease in blood pressure.

8. The method of claim 7, wherein the substance comprises naloxone.

9. The method of claim 6, wherein the hypovolemia diagnostic model corresponds to a decrease in blood pressure, an increase in heart rate, and stability in hemoglobin level.

10. The method of claim 9, wherein the substance comprises saline.

11. The method of claim 6, wherein the sepsis diagnostic model corresponds to a decrease in blood pressure, an increase in white blood cell count, and an increase in temperature.

12. The method of claim 11, wherein initiating the workflow further comprises one or more of the following: alerting a clinician, ordering a lab test, ordering a drug, and ordering a radiology test.

13. An automated first responder system, the system comprising:
   a patient monitor comprising a hardware processor configured to derive physiological parameter values from physiological signals obtained from one or more physiological sensors coupled with a patient; and
   an autonomous delivery device in communication with the patient monitor, the autonomous delivery device comprising at least one substance;
   the hardware processor configured to:
   analyze the physiological parameter values to determine whether the physiological parameter values correspond with a diagnostic model;
   determine that the physiological parameter values correspond with the diagnostic model;
   responsive to said determination, initiate a treatment workflow that automatically administers a substance, based, at least in part, on the diagnostic model, to the patient from the autonomous delivery device;
   subsequent to said administration, analyze the physiological parameter values again and determine that the physiological parameter values again correspond with the diagnostic model; and
   responsive to said determination that the physiological parameter values again correspond with the diagnostic model, send an alert to a clinician over a hospital network, the alert indicating a recommendation that the clinician provide an additional amount of the substance but not automatically providing the additional amount of the substance.

14. The system of claim 13, wherein said analyzing the physiological parameter values comprises identifying a trend in the physiological parameter values and determining whether the trend corresponds with predetermined trends in the diagnostic model.

15. The system of claim 13, wherein the diagnostic model represents one of the following: an opioid overdose diagnostic model, a hypovolemia diagnostic model, or a sepsis diagnostic model.

16. The system of claim 15, wherein the opioid overdose diagnostic model corresponds to a decrease in respiratory rate, a decrease in heart rate, and a decrease in blood pressure.

17. The system of claim 16, wherein the substance comprises naloxone.

18. The system of claim 15, wherein the hypovolemia diagnostic model corresponds to a decrease in blood pressure, an increase in heart rate, and stability in hemoglobin level.

19. The system of claim 18, wherein the substance comprises saline.

20. The system of claim 15, wherein the sepsis diagnostic model corresponds to a decrease in blood pressure, an increase in white blood cell count, and an increase in temperature.

21. The system of claim 20, wherein initiating the workflow further comprises one or more of the following: alerting a clinician, ordering a lab test, ordering a drug, and ordering a radiology test.

* * * * *